US012622886B2

(12) United States Patent
Giorgetti

(10) Patent No.: US 12,622,886 B2
(45) Date of Patent: May 12, 2026

(54) COMPOSITIONS COMPRISING AMINO ACIDS FOR PREVENTION AND/OR TREATMENT OF CANCER

(71) Applicant: Professional Dietetics S.p.A., Milan (IT)

(72) Inventor: Paolo Luca Maria Giorgetti, Milan (IT)

(73) Assignee: PROFESSIONAL DIETETICS S.P.A., Milan (IT)

( * ) Notice: Subject to any disclaimer, the term of this patent is extended or adjusted under 35 U.S.C. 154(b) by 956 days.

(21) Appl. No.: 17/792,249

(22) PCT Filed: Dec. 21, 2020

(86) PCT No.: PCT/IB2020/062301
§ 371 (c)(1),
(2) Date: Jul. 12, 2022

(87) PCT Pub. No.: WO2021/144640
PCT Pub. Date: Jul. 22, 2021

(65) Prior Publication Data
US 2023/0079527 A1     Mar. 16, 2023

(30) Foreign Application Priority Data
Jan. 13, 2020     (IT) ........................ 102020000000454

(51) Int. Cl.
*A61K 31/198*          (2006.01)
*A61K 31/194*          (2006.01)

(52) U.S. Cl.
CPC .......... *A61K 31/198* (2013.01); *A61K 31/194* (2013.01)

(58) Field of Classification Search
CPC ............................ A61K 31/198; A61K 31/194
See application file for complete search history.

(56) References Cited

U.S. PATENT DOCUMENTS

| | | |
|---|---|---|
| 6,537,969 B1 | 3/2003 | Blass |
| 7,982,066 B2 | 7/2011 | Scheele |
| 9,597,367 B2 | 3/2017 | Wolfe et al. |
| 10,226,441 B2 | 3/2019 | Higashi et al. |
| 11,337,946 B2 | 5/2022 | Giorgetti |
| 11,452,702 B2 | 9/2022 | Giorgetti |
| 11,957,651 B2 | 4/2024 | Giorgetti |
| 12,239,622 B2 | 3/2025 | Giorgetti |
| 2003/0013761 A1 | 1/2003 | Joshi |
| 2003/0055099 A1 | 3/2003 | Martynyuk et al. |
| 2013/0084378 A1 | 4/2013 | Jun et al. |
| 2013/0237605 A1 | 9/2013 | Zemel |
| 2014/0243400 A1 | 8/2014 | Mcgill |
| 2014/0315788 A1 | 10/2014 | Wolfe |
| 2015/0335627 A1 | 11/2015 | Yue et al. |
| 2016/0038565 A1 | 2/2016 | Khan |
| 2018/0000764 A1 | 1/2018 | Hernández Miramontes |

| | | |
|---|---|---|
| 2020/0230093 A1 | 7/2020 | Giorgetti |
| 2020/0253906 A1 | 8/2020 | Giorgetti |
| 2021/0260011 A1 | 8/2021 | Giorgetti |
| 2022/0110899 A1 | 4/2022 | Giorgetti |
| 2022/0249418 A1 | 8/2022 | Giorgetti |
| 2023/0067642 A1 | 3/2023 | Giorgetti |
| 2023/0079527 A1 | 3/2023 | Giorgetti |

FOREIGN PATENT DOCUMENTS

| | | |
|---|---|---|
| CA | 2972889 A1 | 9/2016 |
| CN | 105982914 A | 10/2016 |
| EP | 2196203 A2 | 6/2010 |
| EP | 2676664 A1 | 12/2013 |
| EP | 2881112 A1 | 6/2015 |
| GB | 2029220 A | 3/1980 |
| JP | H0873351 A | 3/1996 |
| JP | 2007161642 A | 6/2007 |
| JP | 6023813 B2 | 10/2016 |
| WO | 2001051047 A | 7/2001 |
| WO | 2003013487 A1 | 2/2003 |
| WO | 2005034932 A2 | 4/2005 |
| WO | 2006046746 A1 | 5/2006 |
| WO | 2007049818 A1 | 5/2007 |
| WO | 2012040707 A2 | 3/2012 |
| WO | 2012147901 A1 | 11/2012 |
| WO | 2016093104 A1 | 6/2016 |
| WO | 2016116580 A1 | 7/2016 |
| WO | 2016179657 A1 | 11/2016 |
| WO | 2016181335 A1 | 11/2016 |
| WO | 2017020121 A1 | 2/2017 |
| WO | 2017089612 A1 | 6/2017 |
| WO | 2018201024 A1 | 11/2018 |
| WO | 2019/021135 | 1/2019 |
| WO | 2019021137 A1 | 1/2019 |

(Continued)

OTHER PUBLICATIONS

Schafer et al. Drug Discovery Today 2008, 13 (21/22), 913-916 (Year: 2008).*
Horig et al. Journal of Translational Medicine 2004, 2(44) (Year: 2004).*
Bianchi et al. (Current Opinion in Cell Biology. 2020; 63:135-143) (Year: 2020).*
Boshuizen et al. (Molecular Cell. 2020;78:1002-1018) (Year: 2020).*
MedlinePlus. Types of Chemotherapy. https://medlineplus.gov/ency/patientinstructions/000910.htm#:~: text=There%20are%20more%20than%20100,from%20typical%20chemotherapy%20side%20effects) (Year: 2023).*
Pantuck et al. (Anesth Analg. 1989; 69: 727-731) (Year: 1989).*
Bonfili et al. (The FEBS Journal. 2017; 284: 1726-1737) (Year: 2017).*
Fakouri et al. (Biology. 2019;8(2): 3). (Year: 2019).*

(Continued)

*Primary Examiner* — Clinton A Brooks
*Assistant Examiner* — Jerica Katlynn Wilson
(74) *Attorney, Agent, or Firm* — Nixon & Vanderhye, PC

(57) ABSTRACT

Composition for use in the prevention and/or treatment of cancer in a subject, the composition comprising an active agent, said active agent containing the amino acids leucine, isoleucine, valine, threonine, lysine and citric acid, 5succinic acid, malic acid.

17 Claims, 7 Drawing Sheets

(56) References Cited

FOREIGN PATENT DOCUMENTS

| WO | 2019070750 A1 | 4/2019 |
| WO | 2019165321 A1 | 8/2019 |
| WO | 2020/003013 | 1/2020 |
| WO | 2022023932 A1 | 2/2022 |
| WO | 2022266480 A1 | 12/2022 |

OTHER PUBLICATIONS

Demarco, C. MDAndersonCancerCenter.2021. 'https://www.mdanderson.org/cancerwise/adenocarcinomas--6-things-to-know-about-the--cancer-of-the-cavities.h00-159465579.html#:~: text=That%20being%20said%2C%20chemotherapy%20is,fantastic%20advance%20in%20early%20detection. (Year: 2021).*

International Search Report and Written Opinion of the ISA for PCT/IB2020/062301 dated Mar. 1, 2021 (12 pages).

Wang, X. et al., "Increases in mitochondrial biogenesis impair carcinogenesis at multiple levels" Molecular Oncology, Elsevier. Jul. 27, 2011., vol. 5, No. 5, pp. 399-409 (11 pages).

Abdullah, Chowdhury S. et al., "Doxorubicin-induced cardiomyopathy associated with inhibition of autophagic degradation process and defects in mitochondrial respiration", Scientific Reports, vol. 9, No. 1, Feb. 14, 2019, 20 pp.

Anonymous: "Amino acid-derived therapy for Inflammatory bowel disease: L-Leucine, the branched chain amino acid, promotes NFKB-p50/p65 dimer formation, induces inflammatory gene expression downstream of RelA/p65, inhibits colonic pathogenesis, and stalls the progression of inflammatory bowel disease and colitis", May 16, 2017, XP093023862, 5 pages, retrieved from the Internet: URL: https://genomediscovery.org/natural-product-derived-therapy-for-inflammatory-bowel-disease-1-leucine-the-branched-chain-amino-acid-promotes-nfkb-p50p65-dimer-formation-induces-inflammatory-gene-expression-downstream-of-rel/.

Ashida, Toshifumi et al., "Effect of Oral Administration of Isoleucine, Stimulant of Innate Immunity, in IBD Patients", Gastroenterology, vol. 26, No. 4, Suppl 2, Apr. 1, 2004, 1 page, XP093023803, retrieved from the Internet: URL:https : //www.gastrojournal.org/issue/S0016-5085(00)X0347-2.

Balaraman Kalyanaraman, "Teaching the basics of the mechanism of doxorubicin-induced cardiotoxicity: Have we been barking up the wrong tree?" Redox Biology, 29: 101394 (2020).

Beale et al., A Randomized Clinical Trial of High-Dosage Coenzyme Q10 in Early Parkinson Disease No Evidence of Benefit, JAMA Neurol., 71(5), pp. 543-552, 2014.

Bournat, J.C., et al., Mitochondrial Dysfunction in Obesity Current Opinion Endocrinol Obesity, October, 17(5): 446-452, 2010.

Brocca et al., "Proteomic analysis of plasma after branched chain enriched mixture supplementation in mice", Journal of the International Society of Sports Nutrition, vol. 10, No. 1, Apr. 3, 2013, 5 pages.

Brown et al., Mitochondrial function as a therapeutic target in heart failure, Nat Rev Cardiol., 14(4), pp. 238-250, 2017.

Chiechio, et al., "L-Acetylcarnitine: A Proposed Therapeutic Agent for Painful Peripheral Neuropathies", Current Neuropharmacology, vol. 4, No. 3, Jul. 1, 2006, pp. 233-237 (5 pages).

Choudhury, Aaheli Roy et al., "Mitochondrial determinants of cancer health disparities", Seminars in Cancer Biology, 47, 2017, pp. 125-146.

Daher et al., J Clin Transl Hepatol. Mar. 28, 2018;6(1 ):69-78 (Year: 2018).

Damiani, Roberto Marques et al., "Pathways of cardiac toxicity: comparison between chemotherapeutic drugs doxorubicin and mitoxantrone", Archives of Toxicology, vol. 90, No. 9, Jun. 25, 2016, pp. 2063-2076.

Database WPI Week Apr. 4, 2007, May 3, 2007, Thomson Scientific, London, GB, XP002788927, 3 pages.

Fernández-Vizarra, et al., Tissue-specific differences in mitochondrial activity and biogenesis, Mitochondrion, vol. 11, pp. 207-213, 2011.

Gilliam, Laura A.A. et al., "The anticancer agent doxorubicin disrupts mitochondrial energy metabolism and redox balance in skeletal muscle", Free Radical Biology and Medicine, vol. 65, Sep. 7, 2013, pp. 988-996.

Gorshinova et al., "Mitochondrial dysfunction as one of the mechanisms of impaired reproductive function in obesity." Akusherstvo i ginekologiya/Obstetrics and Gynecology. 2014; 7: 9-13. in Russian with English Abstract.

Green et al. (Biochmica et Biophysica Acta 1588 (2002) 94-101 (Year: 2002).

Hall et al., "Lipid Peroxidation in Brain or Spinal Cord Mitochondria After Injury" J Bioenerg. Biomembr. Apr. 2016; 48(2): 169-174 (2017).

Hiensch, Anouk E. et al., "Doxorubicin-induced skeletal muscle atrophy: Elucidating the underlying molecular pathways", Acta Physiologica, vol. 229, No. 2, Oct. 10, 2019, 18 pp.

Keenan et al.,, "Effects of carboxylic acids on the uptake of non-transferrin-bound iron by astrocytes, Neurochemistry International", 2010, 56: 843-849.

Kim, Yun-Gi et al., "Neonatal acquisition of Clostridia species protects against colonization by bacterial pathogens", Science, vol. 356, No. 6335, Apr. 21, 2017, pp. 14 pages.

Liu, Yulan et al., "Roles of amino acids in preventing and treating intestinal diseases: recent studies with pig models", Amino Acids, vol. 49, No. 8, Jun. 14, 2017, pp. 1277-1291.

Ma et al., Inhibition of AMP-Activated Protein Kinase Signaling Alleviates Impairments in Hippocampal Synaptic Plasticity Induced by Amyloid, The Journal of Neuroscience, 34(36), 12230-12238, Sep. 3, 2014.

Mao, Xiangbing et al., "I-Isoleucine Administration Alleviates DSS-Induced Colitis by Regulating TLR4/MyD88/NF-κB Pathway in Rats", Frontiers in Immunology, vol. 12, Article 817583, Jan. 11, 2022, 12 pages.

MP Biomedical—Technical Information—AIN-93-Diet,pp. 1-3 (Year: 2023).

Nakagaichi, M., et al., "Effects of Exercise Training Plus Vespa Amino Acid Mixture (VAAM) Ingestion in Obese Women," Japanese Journal of Health Promotion, 3, Nov. 16, 2001 with English Abstract.

Nakamura, E., et al., "Assessment of Biological Age by Principal Component Analysis," Mechanisms of Ageing and Development, vol. 46. Issues1-3, pp. 1-18, 1988, with English Translation of Office Action for JP Application No. 2019-566744 citing Nakamura attached to satisfy the requirement for a concise explanation of relevance.

Nergiz et al.; "Organic acid content and composition of the olive fruits during ripening and its relationship with oil and sugar"; 2009; Scientia Horticulturae; 122: 216-220 (Year: 2009).

Rao et al., Mitochondrial permeability transition pore is a potential drug target for neurodegeneration, Biochimica et Biophysica Acta, 1267-1272, 2014.

Sbodio et al., Redox Mechanisms in Neurodegeneration: From Disease Outcomes to Therapeutic Opportunities, Antioxidants & Redox Signaling, vol. 30, No. 11, pp. 1450-1499, 2019.

Scholpa & Schnellmann, "Mitochondrial-Based Therapeutics for the Treatment of Spinal Cord Injury: Mitochondrial Biogenesis as a Potential Pharmacological Target." J Pharmacol Exp Ther 363:303-313, Dec. 2017.

Short et al., Decline in skeletal muscle mitochondrial function with aging in humans, PNAS, vol. 102, No. 15, pp. 5618-5623, Apr. 12, 2005.

Sprong et al., "Dietary cheese whey protein protects rats against mild dextran sulfate sodium-induced colitis: Role of mucin and microbiota", Journal of Dairy Science, vol. 93, No. 4, Apr. 1, 2010, pp. 1364-1371.

Sullivan et al., "Mitochondrial Permeability Transition in CNS Trauma: Cause or Effect of Neuronal Cell Death?" Journal of Neuroscience Research, 2005, 79:231-239.

Sun et al., The Mitochondrial Basis of Aging, Mol Cell., 61(5), pp. 654-666, Mar. 3, 2016.

Tapper et al., JAMA. 2023;329(18):1589-1602 (Year: 2023).

Tedesco et al., A specific amino acid formula prevents alcoholic liver disease in rodents, Am J Physiol Gastrointest Liver Physiol ., Epub Jan. 25, 2018, 314(5):G566-G582.

(56) References Cited

OTHER PUBLICATIONS

Vingtdeux et al., AMPK is abnormally activated in tangle- and pre-tangle-bearing neurons in Alzheimer's disease and other tauopathies, Acta Neuropathol, vol. 121, pp. 337-349, 2010.

Wang et al., "Mitochondrial dysfunction in neurodegenerative diseases and the potential countermeasure," CNS Neurosci Ther. 25: 816-824 (2019).

Westermann et al., Mitochondrial fusion and fission in cell life and death, Molecular Cell Biology, vol. 11, 13 pages, Dec. 2010.

Youle et al., Mitochondrial Fission, Fusion, and Stress, Science, 337(6098), pp. 1062-1065, Aug. 31, 2012.

Xu et al., "mTOR signaling in tumorigenesis" Biochim Biophys Acta. Dec. 2014 ; 1846(2): 638-654.

Moberg et al., "Activation of mTORC1 by leucine is potentiated by branched-chain amino acids and even more so by essential amino acids following resistance exercise," Am J Physiol Cell Physiol 310: C874-C884, 2016.

Lee et al., "Mitochondrial DNA plasticity is an essential inducer of tumorigenesis," Cell Death Discovery (2016) 2, 16016; 11 pages.

U.S. Appl. No. 18/878,129; first inventor: Giorgetti, 371(c) date Dec. 23, 2024.

* cited by examiner

DMEM

α5

COMPOSITIONS COMPRISING AMINO ACIDS FOR PREVENTION AND/OR TREATMENT OF CANCER

This application is the U.S. national phase of International Application No. PCT/IB2020/062301 filed Dec. 21, 2020 which designated the U.S. and claims priority to IT 102020000000454 filed Jan. 13, 2020, the entire contents of each of which are hereby incorporated by reference.

FIELD OF THE INVENTION

The present description relates generally to compositions comprising amino acids for use in the prevention and treatment of cancer.

BACKGROUND

Cancers have a different metabolic profile with respect to normal tissues and contrasting evidence are emerging on the role of mitochondrial activity in the proliferation of cancer cells. The so-called Warburg effect, the preferential use of glucose even in presence of oxygen is one of the hallmarks of tumor cells. This phenomenon, initially defined as "aerobic glycolysis" led to the earliest hypothesis of a defective mitochondrial function in cancer. However, this setting has been shown to be more complex, and there is now general agreement that cancer mitochondria, during oncogenesis, engage in pleiotropic functions, such as macromolecular biosynthesis, apoptosis resistance, and activation of oncogenic signaling. Nevertheless, many mitochondrial mutations are indeed found in tumors, and a decreased oxidative phosphorylation (OXPHOS) rate has been shown, owing to a reduction in reactive oxygen species (ROS), to result in a proliferative advantage and an increase in cancer cell proliferation. Furthermore, given the pivotal role of glycolysis pathway in cancer growth, and since OXPHOS and glycolysis are reciprocally regulated, it is tempting to speculate that enhancing mitochondrial function could lead to glycolysis inhibition and cancer cell death. Moreover, much attention and efforts have been employed to develop glycolytic inhibitors as a pharmaceutic approach in anti-cancer therapy; some first and second generation drugs have been developed but their safety profile and development of resistance has raised some concerns.

SUMMARY OF THE INVENTION

The present description has the aim of providing new compositions particularly effective in the prevention and/or treatment of cancer and endowed with a safe administration profile.

According to the present description, the above object is achieved thanks to the subject matter specifically recalled in the ensuing claims, which are understood as forming an integral part of this disclosure.

An embodiment of the present description provides a composition for use in the prevention and/or in the treatment of cancer in a subject, the composition comprising an active agent, said active agent containing the amino acids leucine, isoleucine, valine, threonine, lysine and citric acid, succinic acid, malic acid.

In one or more embodiments, the cancer may be selected in the group consisting of melanoma, adenocarcinoma, colorectal carcinoma, breast cancer.

In one or more embodiments, the active agent of the composition may further contain one or more amino acids selected in the group consisting of histidine, phenylalanine, methionine, tryptophan, cysteine and tyrosine.

BRIEF DESCRIPTION OF THE FIGURES

The invention will now be described, by way of example only, with reference to the enclosed figures, wherein.

DETAILED DESCRIPTION OF PREFERRED EMBODIMENTS

Figure 1:
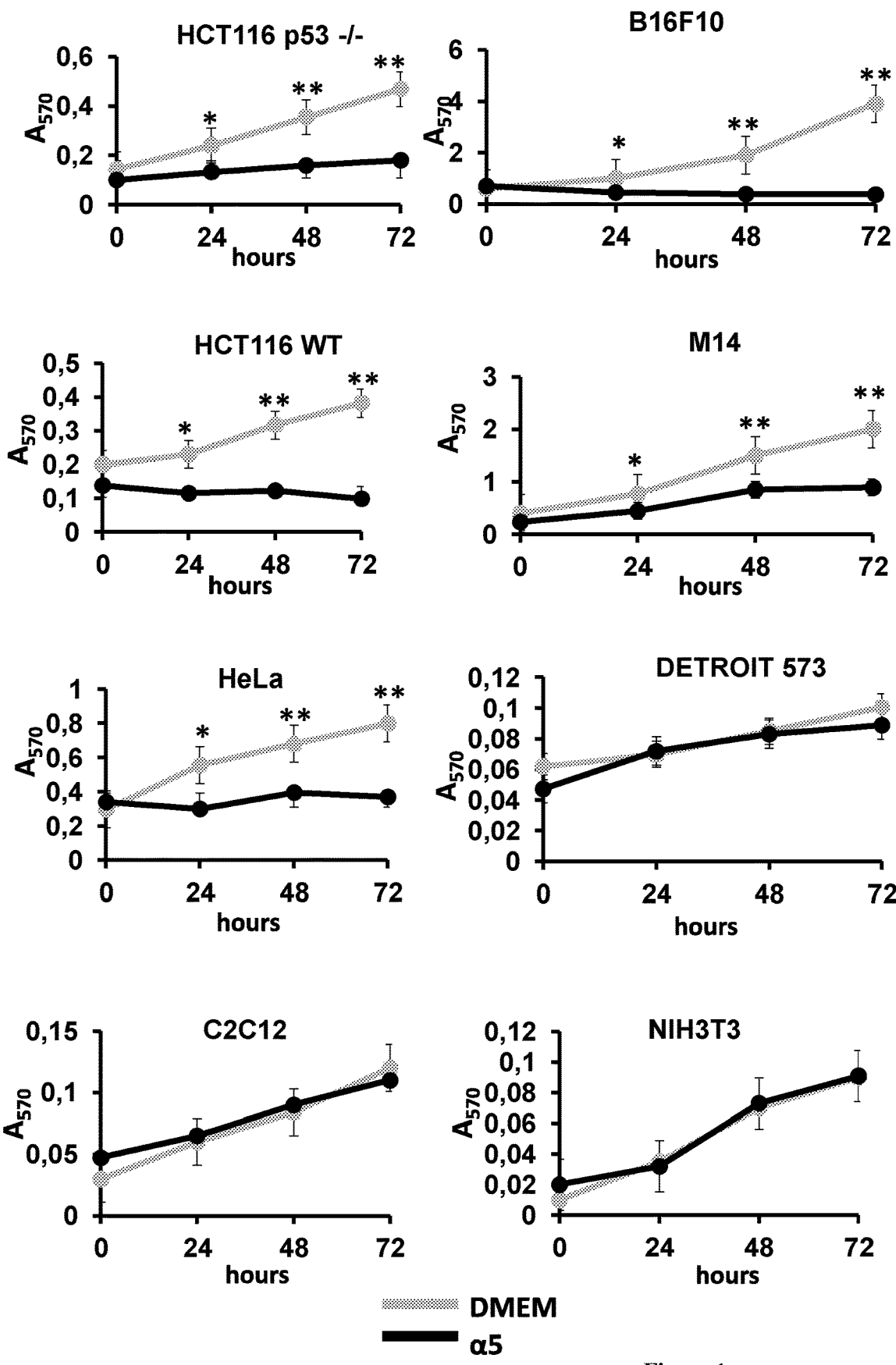
FIG. 1 shows a MTT viability assay in cancer and normal cells incubated for the times indicated, with a normal media (DMEM) or with the composition of the instant application (α5). *$p<0.01$**$p<0.05$ vs DMEM.

In the following description, numerous specific details are given to provide a thorough understanding of embodiments. The embodiments can be practiced without one or more of the specific details, or with other methods, components, materials, etc. In other instances, well-known structures, materials, or operations are not shown or described in detail to avoid obscuring aspects of the embodiments.

Reference throughout this specification to "one embodiment" or "an embodiment" means that a particular feature, structure, or characteristic described in connection with the embodiment is included in at least one embodiment. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments. The headings provided herein are for convenience only and do not interpret the scope or meaning of the embodiments.

An embodiment of the present description provides a composition for use in the prevention and/or treatment of a cancer in a subject, the composition comprising an active agent, said active agent containing the amino acids leucine, isoleucine, valine, threonine, lysine and citric acid, succinic acid, malic acid.

The cancer may be selected in the group consisting of adenocarcinoma, melanoma, colorectal carcinoma, breast cancer.

The disclosure further provides combined preparations comprising the composition herein disclosed and at least one chemotherapeutic agent for simultaneous, separate or sequential use in preventing and/or treating a cancer in a subject.

The Inventor of the instant application has surprisingly found that the composition herein disclosed is particularly effective in reducing the proliferation rate of cancer cells, such as cervical cancer cells, melanoma cells, colon cancer cells, breast cancer cells and has no effect on the rate of proliferation of normal cells. The composition has also been shown to be effective on the inhibition of cancer cell motility and clonogenic potential. Very importantly, the composition exerts an inhibitory effect on the mTOR pathway and this evidence is noteworthy, since an increased mTOR activity is often associated with tumorigenesis and essential amino acid-based compositions are known to activate mTOR pathway.

Moreover, as shown in the following sections, the composition may be safely administered either alone or in combination with at least one chemotherapeutic agent. The chemotherapeutic agents may be for example at least one anthracycline, for example doxorubicin.

In one or more embodiments, the composition herein disclosed comprises an active agent, said active agent contains citric acid, succinic acid and malic acid in combination with leucine, isoleucine, valine, threonine, lysine, and the weight ratio between the total amount of citric acid, succinic acid and malic acid and the total amount of the amino acids leucine, isoleucine, valine, threonine, lysine is comprised between 0.05 and 0.3, preferably between 0.1 and 0.25.

In one or more embodiments, the composition may consist of leucine, isoleucine, valine, threonine, lysine, citric acid, succinic acid and malic acid and optionally vitamin B1 and vitamin B6.

In one or more embodiments, the active agent may further comprise one or more amino acids selected in the group consisting of histidine, phenylalanine, methionine, tryptophan, cysteine, tyrosine.

In one or more embodiments, The composition may comprise an active agent consisting of leucine, isoleucine, valine, threonine, lysine, histidine, phenylalanine, methionine, tryptophan, cysteine and optionally tyrosine, as well as citric acid, succinic acid and malic acid, said amino acids being the sole amino acids contained in the composition.

In one or more embodiments, the composition may be free of any other active agent, such as any chemotherapeutic agent, i.e. any agent that directly or indirectly inhibit the proliferation of rapidly growing cells, exerting an antineoplastic effect.

In one or more embodiments, the composition may consist of leucine, isoleucine, valine, threonine, lysine, histidine, phenylalanine, methionine, tryptophan, cysteine, tyrosine, citric acid, succinic acid and malic acid and optionally vitamin B1 and/or vitamin B6.

The composition may comprise the amino acids isoleucine, leucine and valine in an amount between 35% and 65% by weight, preferably between 42% and 56% by weight with respect to the active agent weight.

The weight ratio between leucine and citric acid may be comprised between 5 and 1, preferably between 2.50 and 3.50.

In a further embodiment, the weight or molar amount of citric acid is higher than the weight or molar amount of each of malic acid and succinic acid. Preferably, the weight or molar amount of citric acid is higher than the weight or molar overall amount of malic acid plus succinic acid. In a further embodiment, the weight ratio between citric acid and the sum of malic acid and succinic acid is comprised between 1.0 and 4.0, preferably between 1.5 and 2.5. In a preferred embodiment, the citric acid:malic acid:succinic acid weight ratio is comprised between 10:1:1 and 2:1.5:1.5, preferably between 7:1:1 and 1.5:1:1, more preferably between 5:1:1 and 3:1:1. In a preferred embodiment the citric acid:malic acid:succinic acid weight ratio is 4:1:1.

The preferred isoleucine:leucine molar ratio is comprised in the range 0.2-0.7, preferably in the range 0.30-0.60 and/or the preferred valine:leucine weight ratio is comprised in the range 0.2-0.70, preferably in the range 0.30-0.65.

In a further embodiment, the threonine:leucine molar ratio is comprised in the range of 0.10-0.90, preferably in the range 0.20-0.70 and/or the lysine:leucine weight ratio is comprised in the range of 0.20-1.00, preferably in the range 0.40-0.90.

In a preferred embodiment, the ratio between the overall molar amount of citric acid, malic acid, succinic acid and the overall molar amount of methionine, phenylalanine, histidine and tryptophan is higher than 1.35.

In one or more embodiments, the weight ratio between the sum of citric acid, malic acid, succinic acid and the sum of the branched chain amino acids leucine, isoleucine, valine is comprised between 0.1 and 0.4, preferably between 0.15 and 0.35.

In a further embodiment, the overall weight amount of the branched chain amino acids leucine, isoleucine, valine plus threonine and lysine is higher than the overall weight amount of the three acids citric acid, malic acid, succinic acid. Preferably, the weight amount of the single acids (citric acid, succinic acid or malic acid) is less than the weight amount of each of the single amino acids leucine, isoleucine, valine, threonine and lysine.

In a further embodiment, the overall molar amount of lysine and threonine is higher than the overall molar amount of the three acids citric acid, succinic acid, malic acid. Preferably, the ratio between the overall molar amount of the three acids citric acid, succinic acid, malic acid and the overall molar amount of lysine and threonine is comprised between 0.1 and 0.7, preferably between 0.15 and 0.55.

In one or more embodiments, the composition herein disclosed further comprises vitamins, preferably selected in the group of vitamins B, such as vitamin B1 and/or vitamin B6. The composition may include carbohydrates, flavouring substances, natural and artificial sweeteners, excipients. The excipients may be selected from maltodextrins, fructose, fish oil, sucralose, sucrose esters, vitamin D3, group B vitamins.

In one or more embodiments, the composition may be a pharmaceutical composition further comprising a pharmaceutically acceptable vehicle and at least one pharmaceutically acceptable excipient as disclosed above.

The amino acids disclosed in the instant description can be replaced by respective pharmaceutically acceptable derivatives, namely salts.

Furthermore, in particular when preparing the compositions according to the instant disclosure, and specifically the active agent, the amino acid arginine is to be avoided. In addition, further amino acids specifically excluded by the composition herein disclosed are serine, proline, alanine. Such amino acids can be counterproductive or even harmful in some concentrations or stoichiometric ratios within the composition.

For oral use, the compositions according to the description may be in the form of tablets, capsules, granules, gel, jellifying powder, powder.

The disclosure also provides a method for preventing and/or treating cancer in a subject, the method comprising selecting a composition comprising an active agent, said active agent containing the amino acids leucine, isoleucine, valine, threonine, lysine, and the carboxylic acids citric acid, succinic acid, and malic acid, and administering the composition to the subject. The active agent may further comprise one or more amino acids selected in the group consisting of histidine, phenylalanine, methionine, tryptophan, cysteine, tyrosine, as disclosed herein. The composition may be administered alone, thus the method consists in selecting the composition and administering the composition to the subject. In one or more embodiments, the composition may also be administered—simultaneously, separately or sequentially—with at least one chemotherapeutic agent, preferably at least one anthracycline, more preferably said at least one anthracycline being selected in the group consisting of doxorubicin, epirubicin, daunorubicin, idarubicin, pixantrone, sabarubicin, valrubicin, derivatives thereof.

Further specifications, in terms of amounts and ratios among the various amino acids provided for by the compositions are contained in the attached claims, which form an integral part of the technical teaching provided herein in relation to the invention.

EXAMPLES

Table 1 shows the composition disclosed in the instant application (named "α5"). The composition comprises an active agent containing amino acids in combination with citric acid, succinic acid and malic acid and it is free of any chemotherapeutic agents.

TABLE 1

| Composition (% w/w) | α5 |
| --- | --- |
| L-Leucine | 31.0885 |
| L-Lysine HCl chlorhydrate | 16.9030 |
| L-Isoleucine | 10.3628 |
| L-Valine | 10.3628 |
| L-Threonine | 7.2540 |
| L-Cysteine | 3.1089 |
| L-Histidine | 3.1089 |
| L-Phenylalanine | 2.0726 |
| L-Methionine | 1.0363 |
| L-Tyrosine | 0.6218 |
| L-Tryptophan | 2.0726 |
| Citric acid | 8.001 |
| Succinic acid | 2.00 |
| Malic acid | 2.00 |
| Vitamin B1 (thiamine chlorhydrate) | 0.004 |
| Vitamin B6 (piridoxine chlorhydrate) | 0.0038 |

The composition of Table 1 above may be prepared first by sifting all the components with a 0.8 mesh. To obtain a pre-mixture, each ingredient (in an amount <10% by weight of the total amount) is put in a polyethylene bag together with a portion of L-lysine HCl so as to obtain 10% of the weight of the total composition. The bag is then manually shaken for 5 minutes. The pre-mixture is then loaded in a mixer (*Planetaria*) together with the remainder of the ingredients and mixed for a period of 15 minutes at 120 rpm to obtain a homogeneous final composition.

Methods

Cells and Treatments

Cell lines used were: B16F10 (mouse melanoma, ATCC #CRL-6475), C2C12 (mouse myoblasts, ATCC #CRL-1772), HeLa (human adenocarcinoma, ATCC #CCL-2), Detroit 573 (human fibroblasts, ATCC #CCL-117), NIH3T3 (mouse embryonic fibroblasts, ATCC #CRL-1658), MCF-7 (human breast cancer cell line, ATCC #HTB-22), HCT116 (human colorectal carcinoma cells ATCC #CCL-247), M14 (human melanoma) [Chee D O et al. 1976 Cancer Res. 36(4):1503-9], HCT116 TP53 (−/−) (p53 null human colorectal carcinoma cells) [Sur S et al. 2009 Proc Natl Acad Sci USA. 10; 106 (10)], HL-1 (mouse cardiomyocytes) [Sigma-Aldrich (Milan, Italy) (SCC065)].

Cells were routinely grown in standard Dulbecco's modified eagle medium (DMEM) supplemented with 4 mM glutamine, 10% fetal bovine serum (FBS) and 100 units/ml penicillin/streptomycin (all reagents from Sigma-Aldrich, Milan, Italy) until 80% confluency. For α5 treatments, cells were incubated for the indicated periods in complete DMEM or with a 1% solution of α5 mixture dissolved in the same medium.

Figure 7:
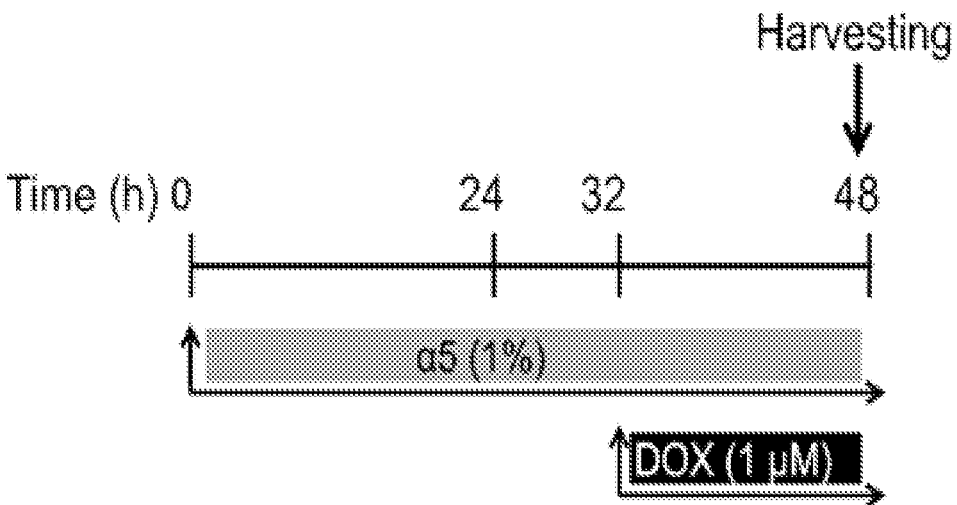
FIG. 7 is relative to MCF7 breast cancer cell proliferation. (A) Acid phosphatase assay: cells (5,000-20,000/well in 96-well plates) were treated with 1% α5 composition for 48 h and 1 µM doxorubicin (DOX) for 16 h. (B) Proliferation assay: cells (50,000/well in 12-well plates) were treated as in (A) and Trypan blue exclusion assay was used. n=3 experiments. *$p<0.05$ and **$p<0.01$ vs. untreated cells. All data are presented as the mean±SD.
Figure 7:
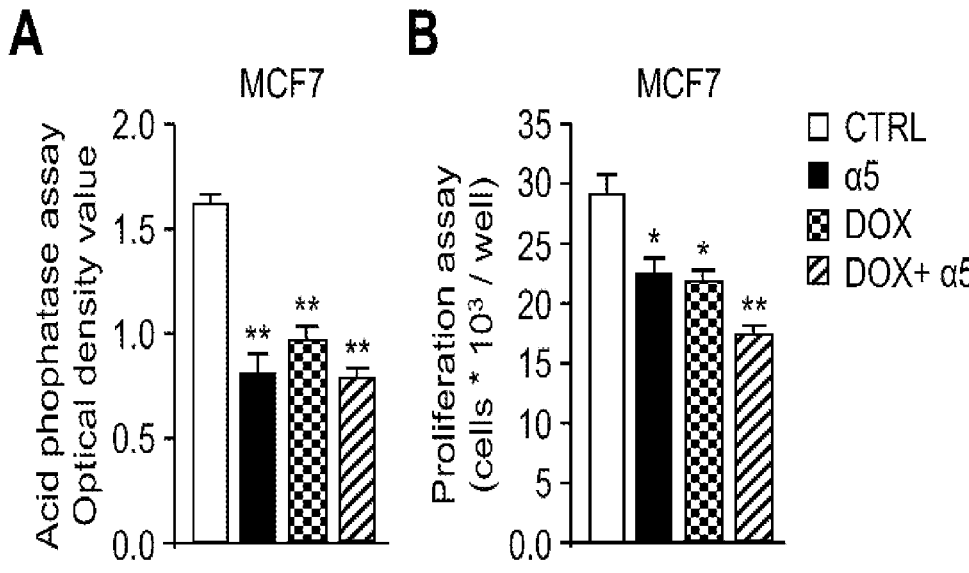

MCF-7 cells were cultured in DMEM as above and treated with 1% α5 composition for 48 h and 1 μM doxorubicin (DOX; Sigma-Aldrich, Milan, Italy) for 16 h (FIG. 7).

Viability Assay

The viability of cells was determined using the standard MTT [3-(4,5-dimethylthiazol-2-yl)-2,5-diphenyltetrazolium bromide] assay. All the treatments were done using $2 \times 10^4$ cells/well in 96 wells plate in 100 μL of medium. The purple formazan crystals were dissolved in 5% SDS/0.1M HCl (100 μL/well), and the absorbance was recorded on a microplate reader at a wavelength of 570 nm.

Monolayer Wound Healing Assay

Cells were grown to full confluence in 24-well plates in their growth media and then were incubated overnight in control or in a α5-containing media. Cell cultures were then scratched with a 200 μL sterile pipette tip and extensively washed with PBS to remove detached cells and debris. To assess migration ability recovery, microscopy images were then collected after 16-24 hrs.

Clonogenic Survival Assay 100 to 1000 cells were seeded in triplicate in six-well plates one day before treatment with control DMEM or α5 composition. Cells were then allowed to grow in DMEM or α5 media until they formed colonies for about 10 days. Survived colonies were fixed with 100% methanol and stained with methylene blue in methanol. At least three biological independent experiments were performed.

Western Blot Analysis

Whole cell extracts were isolated using Lysis Buffer (20 mM Tris-HCl pH 8.0, 400 mM NaCl, 5 mM EDTA, 1 mM EGTA, 1 mM Na pyrophosphate, 1% Triton X-100, 10% glycerol) supplemented with protease and phosphatase inhibitors. The concentration of the isolated proteins was determined using BCA Protein Assay Fifteen-twenty micrograms of the protein were separated on a 4-20% Tris-glycine gel and electrophoretically transferred to nitrocellulose or PVDF membranes (Bio-Rad, Segrate (MI)—Italy). After incubation with 5% nonfat dry milk in TBS-T (10 mM Tris, pH 8.0, 150 mM NaCl, 0.1% Tween 20) for 60 min, the membrane was washed once with TBS-T and incubated with the appropriate antibodies at 4° C. for 12 h. Membranes were washed three times for 10 min and incubated with a 1:3000 dilution of horseradish peroxidase-conjugated anti-mouse or anti-rabbit antibodies for 2 h. Blots were washed with TBS-T three times and developed with the ECL system. Antibodies used were: p-p70S6K (Thr389) (Cell Signaling cat #9205), p70S6K (Cell Signaling cat #9202), HIF1-α (BD Biosciences cat #610958), GAPDH (Cell Signaling cat #2118), CytC (Cell Signaling cat #4280), COXIV (Cell Signaling cat #4844), PARP (Trevigen #4338), Caspase 3 (Cell Signaling cat #9662)

Oxygen Consumption Rate (OCR) and Extracellular Acidification Rate (ECAR) Measurement The rate of change of dissolved 02 (oxygen consumption rate, OCR) and rate of change of pH (extracellular acidification rate, ECAR) was measured in the XF24 Analyzer (Seahorse Biosciences) following manufacturer's instructions.

Cells ($2\text{-}4\times10^3$ per well) were plated in XF24 cell culture microplates (Seahorse Biosciences, MA, USA) and, after 18 hrs, were equilibrated with DMEM lacking bicarbonate (Seahorse Biosciences) supplemented with glucose at 37° C. for 1 h in an incubator lacking $CO_2$. After basal OCR measurement, the compounds oligomycin (2 μM), the uncoupler Carbonyl cyanide (trifluoromethoxy)-phenylhydrazone (FCCP) (1 μM) and the electron transport inhibitors rotenone and antimycin A (R/A) (both 0.5 μM) were then injected into the wells to monitor uncoupled, maximal and non-mitochondrial respiration, respectively. Compound were injected into the wells at the indicated times.

Acid Phosphatase Assay

To quantify MCF7 cell growth, acid phosphatase assay was used as described [Yang T T et al. 1996 Anal Biochem. 241(1):103-8]. Briefly, MCF7 cells were placed in 96-well plates at 5,000 to 20,000 cells per well density and treated with 1% α5 (for 48 h) and 1 μM DOX (for 16 h). Culture medium was removed and each well washed once with phosphate-buffered saline (PBS, pH 7.2), and added with 100 μl buffer containing 0.1 M sodium acetate (pH 5.0), 0.1% Triton X-100, and 5 mM p-nitrophenyl phosphate (pNPP). Then, plates were placed in a 37° C. incubator for 2 h. The reaction was stopped with the addition of 10 μl 1 N NaOH, and color development was assessed at 405 nm. Non-enzymatic pNPP hydrolysis was measured in wells without cells.

Statistical Analysis

Pairwise comparisons between means of different groups were performed using a Student t-test (two tailed, unpaired, unpaired). Data were considered significant with p<0.05.

Results

Inhibitory Effect of the α5 Composition on the Proliferation, Motility and Clone Formation Ability of Cancer Cells The effect of the α5 composition administration was first tested on in vitro cancer cell proliferation. To this end, various cancer cell lines were incubated with the α5 composition (1%). As shown in FIG. 1, α5 composition decreased cancer cell growth with respect to cells grown in culture with control medium only. Most importantly, α5 treatment did not affect growth of normal non-cancer cells. It should be noted that α5 reduced viability of both HCT116 wild-type (WT) and p53–/–, thus demonstrating its effectiveness also in absence of p53; since p53, which is one of the most important tumor suppressor genes, is mutated and inactive in many tumors, this data therefore greatly enlarges the range of action of α5.

Of note, α5 mixture was able to inhibit cancer cell growth as early as 24 hr after starting of treatment. This rapid effect was particularly pronounced in both WT and p53–/– HCT116 cells and Hela (49%, 44% and 46% inhibition, respectively); the growth inhibitory effect of α5 then further increased at 48 hrs, and, by 72 hrs, reached 74%, 61% and 70% of inhibition. The mixture was, however, also effective on both human and mouse melanoma cells; in particular, at 72 hr, α5 inhibited mouse B16F10 mouse melanoma growth by 87%.

Figure 2:
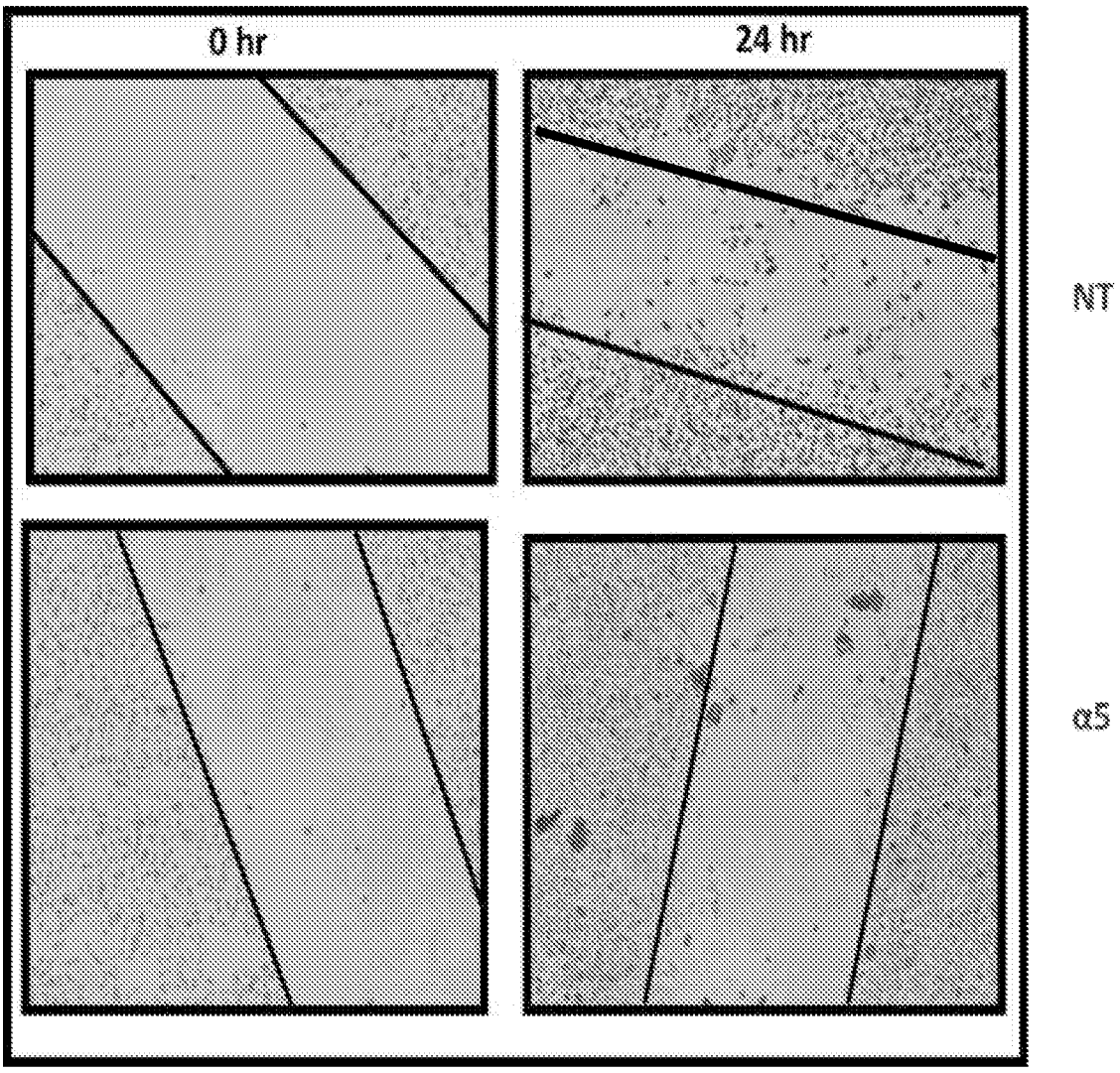
FIG. 2 shows a scratch wound assay in B16F10 melanoma cells at zero (0) hours and incubated for 24 hours (hr) in DMEM (NT) or with the α5 composition (α5).

The administration of the α5 composition also reduced cancer cell motility, as assessed by scratch-wound assay in B16F10. Confluent cells were scratched (0 hr) and then incubated in control media or α5 composition. As shown in FIG. 2, 24 hrs after scratching, cells incubated in control media resumed proliferation and motility, while those incubated in α5 did not, thus showing reduced migration ability.

Figure 3:
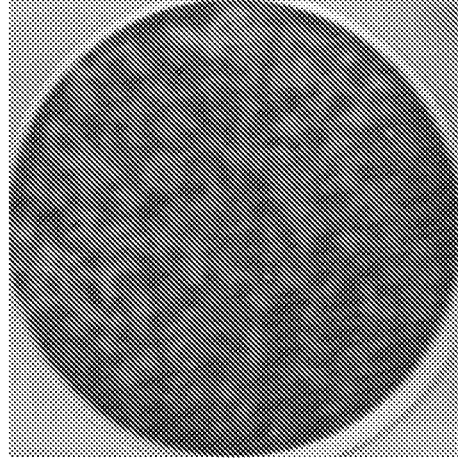
FIG. 3 shows a colony formation assay in HeLa cells incubated for 24 hr in DMEM (NT) or in the α5 composition (α5).
Figure 3:
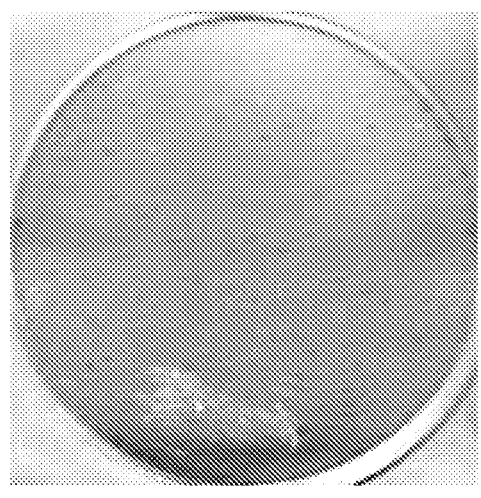

Furthermore, α5 composition also completely blocked clone formation ability in HeLa cells, when single-cell clonogenic potential was challenged in a colony formation assay. As shown in FIG. 3, while cells incubated in control medium efficiently formed single cell-derived colonies during ten days of growth, incubation in α5 composition greatly reduced the ability of HeLa cells to form colonies, therefore confirming that α5 blocks cancer cell reproductive capacity and cancer ability to undergo unlimited division.

The α5 Composition Promotes Apoptotic Cell Death of Cancer Cells

To assess if the reduction in cell proliferation observed was due to a block in cell division or to induction of cell death, various apoptotic markers were analysed in M14 melanoma. It is well-known that, during apoptosis, the mitochondrial protein cytochrome C (CytC) is released into cell cytosol; to this aim, M14 cells were incubated in control or α5 media for 24 hr and thereafter, cell fractionation was performed by separating mitochondria (mito) from cytosolic fraction (Post-mitochondrial supernatant—PMS). CytC localization was then assessed by performing western blot analysis on both mitochondria and PMS. As a control, aimed to verify that release of CytC into the PMS was the specific result of apoptosis and not the consequence of mitochondrial damage (i.e. during fractionation process), localization of Cytochrome oxidase 4 (Cox4), which is not released during apoptosis, was also assessed.

Figure 4:
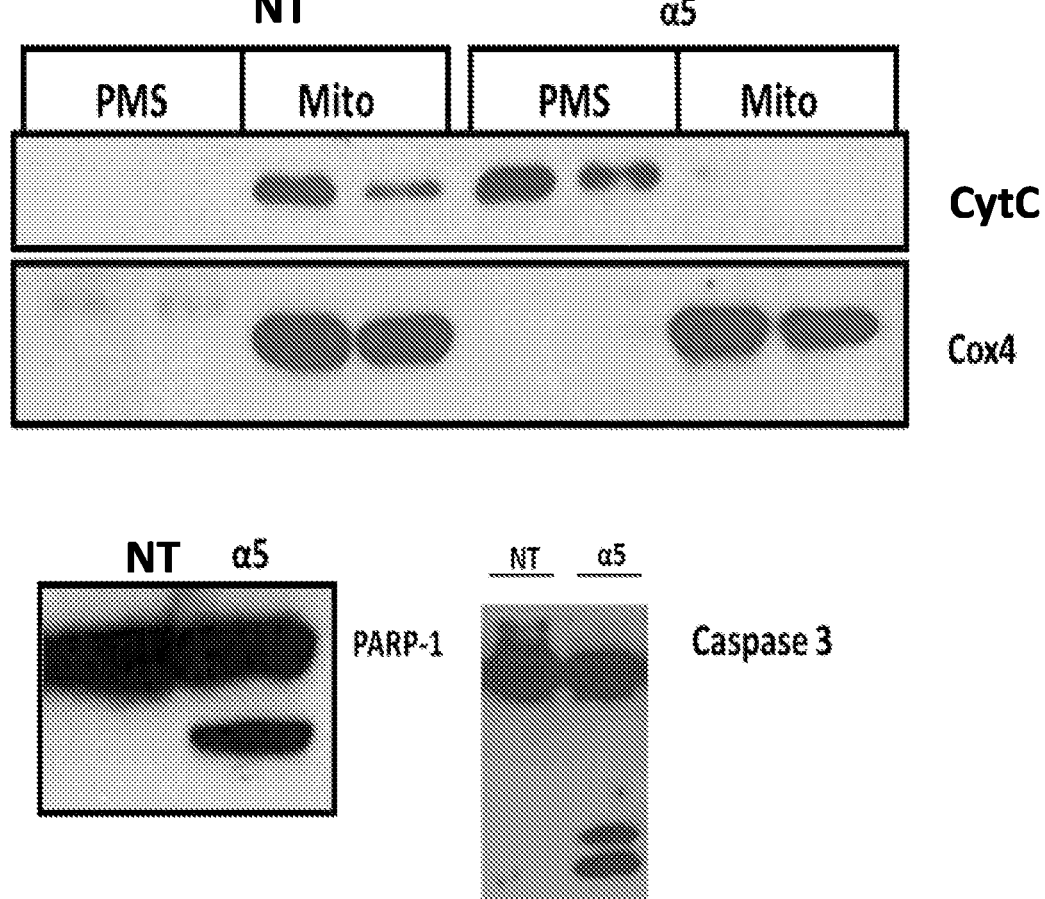
FIG. 4 shows the results of western blot analysis of Cytochrome C (CytC) translocation and apoptosis markers in M14 melanoma cells incubated for 24 hr in DMEM (NT) or in the α5 composition (α5). TOP: α5 induces specific CytC, but not COX4, translocation in cytosol (PMS) of treated cells. BOTTOM: PARP-1 and caspase 3 cleavage in M14 cells.

As shown in FIG. 4, immunoblot analysis showed specific CytC, but not Cox4, translocation in PMS of M14 cells incubated in α5 for 24 hr. Furthermore, clear Parp-1 cleavage, another well-known apoptotic marker, was evident after 24 hr of α5 composition treatment in M14 melanoma cells. In addition, 24 hr of α5 composition also induced cleavage and formation of pro-apoptotic caspase 3 in M14 melanoma cells (FIG. 4).

These results strongly support the evidence that the α5 composition promotes apoptotic cell death of cancer cells.

Inhibitory Effect of the α5 Composition on the Expression of Phospho-p70S6k and HIF1α

One major target of intracellular amino acids is the mechanistic target of rapamycin (mTOR) pathway, a main regulator of cell growth and division that integrates nutrient signals with induction of protein synthesis and cell growth by phosphorylating its downstream effector p70S6 kinase.

Since mTOR pathway is dysregulated in several cancers and its activation is frequently associated with the oncogenic cellular processes, thus enhancing tumorigenicity, the Inventor of the instant application also investigated the p70S6 phosphorylation status as readout of mTOR activity in cancer cells treated with the standard culture medium DMEM or with the α5 composition.

Figure 5:
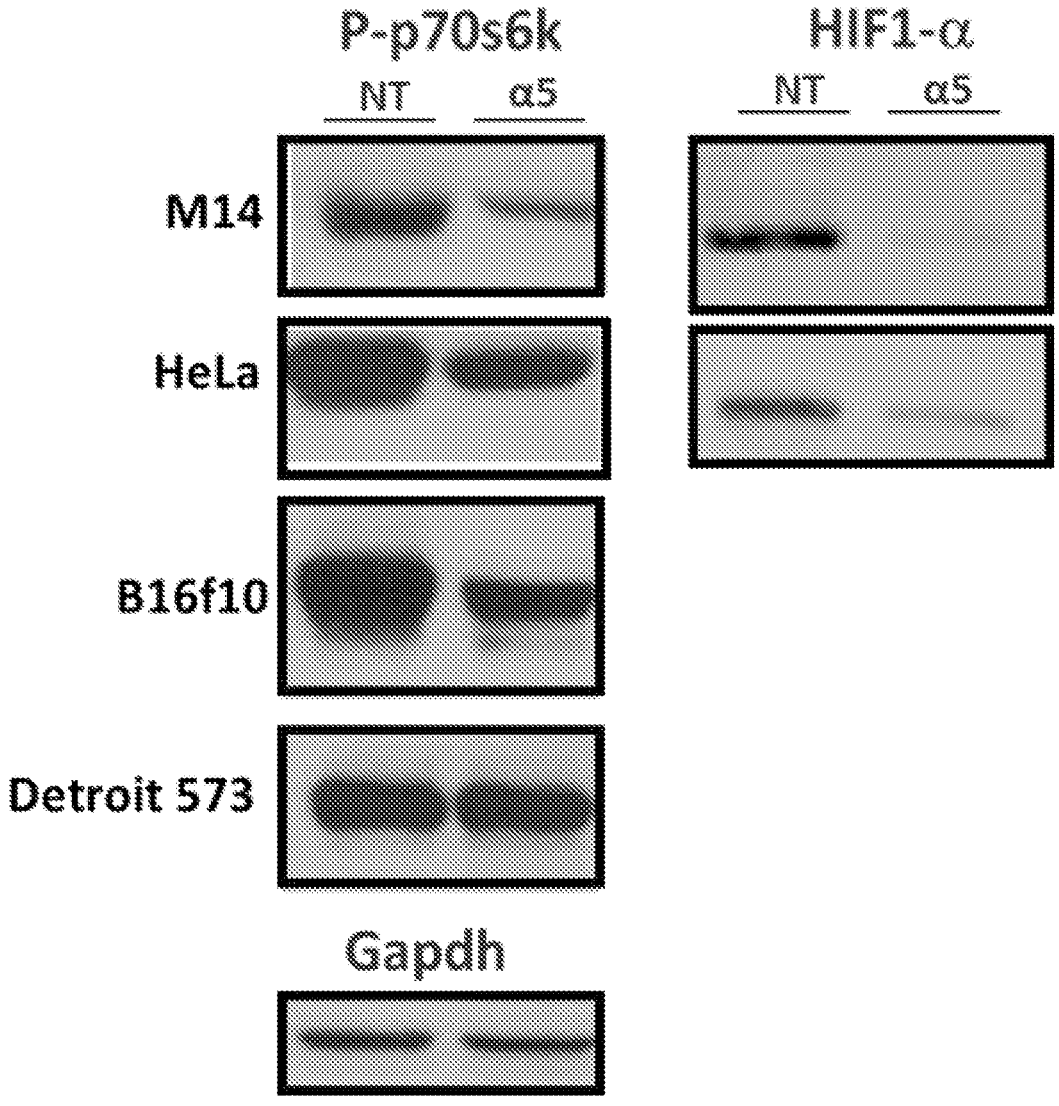
FIG. 5 shows the results of western blot analysis of mTOR pathway and HIF1α in cells incubated for 5 hr in DMEM (NT) or in the α5 composition (α5). LEFT: phospho-p70S6K (thr386) levels, as a marker of mTOR activity in M14, Hela, B16F10 and Detroit 573 fibroblasts. RIGHT: HIF1α expression in M14 and Hela cells. GAPDH is shown as a loading control.

As shown in FIG. 5, p70S6 kinase phosphorylation levels were reduced in α5 treated M14, HeLa and B16F10 cells with respect to cells incubated in standard culture medium (column "NT" or "Non Treated" in FIG. 5); these results indicate the α5 composition surprisingly exerted an inhibitory effect on the mTOR pathway, thus ruling out its activation. Very interestingly, the p70S6k phosphorylation was not affected in normal Detroit 573 cells.

Most importantly, the α5 composition also downregulated, in both M14 and HeLa cells, the expression levels of the hypoxia-inducible factor 1 alpha (HIF1α), which is one of the most important oncogenes involved in tumorigenesis (FIG. 5).

Figure 6:
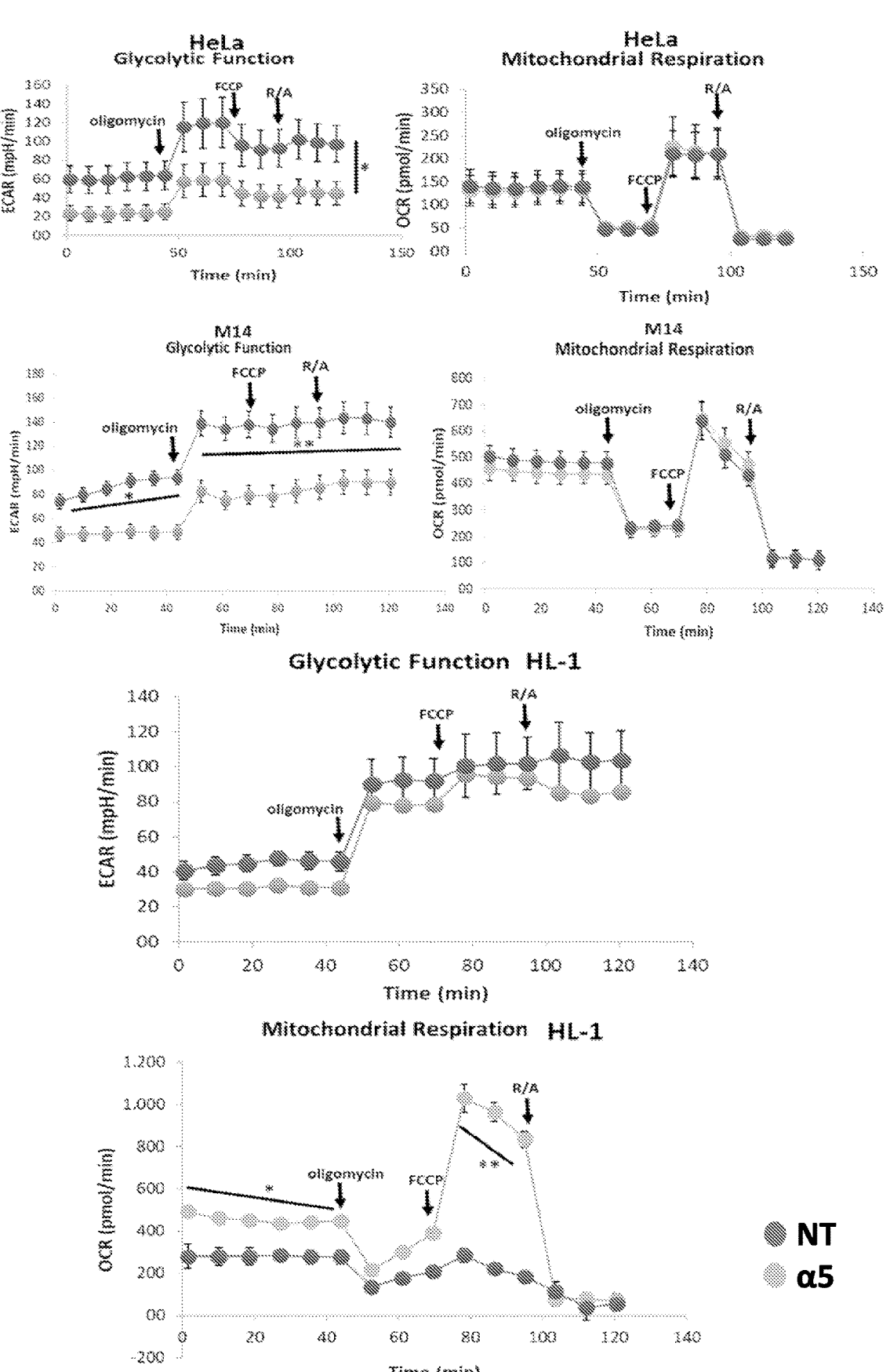
FIG. 6 shows the metabolic activity in cancer cell and in normal cells. Glycolysis (LEFT) and OCR (RIGHT) in HeLa, M14 and HL-1 cells after 1 hour of treatment with DMEM (NT) or in the α5 composition (α5). *$p<0.01$ vs NT.

Since as a major oncogene HIF1α is also a pivotal regulator of cancer glycolysis, the extracellular acidification rate (ECAR) was analyzed, as a measure of the glycolytic rate, in both cancer and normal cells, untreated (NT) or incubated with the α5 composition for 1 hour. As shown in FIG. 6, the treatment with the α5 composition significantly downregulated basal ECAR in cancer cells (p<0.01 vs NT), while slightly decreasing glycolysis in control (NS), non tumor HL-1 cardiomyocytes. However, OCR was not upregulated in M14 and HeLa, while was greatly increased in HL-1 control cardiomyocytes (p<0.01 vs NT).

These data demonstrate that acute α5 composition blocks glycolysis in cancer cells while simoultanesly increases OCR only in normal cells.

The Anti-Proliferative Effect of DOX is Potentiated in the MCF7 Breast Cancer Cells in the Presence of the α5 Composition The effect of the exposure of MCF7 breast cancer cell line to the α5 composition alone or in combination with doxorubicin (DOX) was assessed with two different assays (FIGS. 13A and 13B). The anti-proliferative effect of DOX in MCF7 cells was completely unaffected by the amino acid presence (FIGS. 13A and 13B): very interestingly, the anti-proliferative effect on cancer cell is potentiated when DOX is administered together with the α5 composition.

Altogether the results show that the composition herein disclosed is able to block cancer cell proliferation. Of note, the effect is specific for cancer cells, as normal cells proliferation was unaffected by the α5 composition, with a substantial safety profile and lack of toxic side effects.

Most importantly, the α5 composition exerts an inhibitory effect on the mTOR pathway, as assessed by reduced phosphorylation (activity) of its downstream target p70S6K. Again, this is noteworthy, since increased mTOR activity is often associated with tumorigenesis and essential amino acid-based compositions are known to activate mTOR pathway.

The composition herein disclosed comprises specific amino acids and trycarboxylic acids (TCA cycle intermediates); the administration of the composition may boost the mitochondrial activity and OCR and, as a consequence, shift the metabolic activity away from glycolysis towards amino acids and TCA cycle intermediates oxidation, leading to glycolysis downregulation.

Very surprisingly, although effectively inhibiting glycolysis in cancer cells, such a switch occured only in non cancer cells (as shown in FIG. 6). This result could be ascribed to the extreme sensitivity of cancer cells to glycolysis, whose fast inhibition exerted by the α5 composition, most probably activates the onset of apoptosis before any switch to OCR could take place.

Therefore, the composition of the instant application has been shown to be effective in reducing the proliferation rate of cancer cells without presenting side effects.

The composition may be used alone or also in combined preparations with at least one chemotheraupetic agents; the results herein provided show that when administered together with doxorubicin, the rate of cancer cell proliferation is further reduced. Therefore, the effect of combined therapies also allows to greatly reduce dosage of chemotherapic drugs, thus leading to a more efficient and safe anticancer approach.

The invention claimed is:

1. A method of treating cancer in a subject, the method comprising administering to the subject a therapeutically effective amount of an active agent, said active agent comprising leucine, isoleucine, valine, threonine, lysine, and citric acid, succinic acid, and malic acid, wherein the active agent is free of arginine, serine, proline, and alanine, and wherein said cancer is selected from the group consisting of adenocarcinoma, melanoma, colorectal carcinoma and breast cancer.

2. The method according to claim 1, wherein the weight ratio between (i) the sum of citric acid, malic acid, and succinic acid and (ii) the sum of leucine, isoleucine, valine, lysine, and threonine is comprised between 0.05 and 0.3.

3. The method according to claim 1, wherein the weight ratio between (i) the overall amount of citric acid, malic acid, and succinic acid and (ii) the overall amount of leucine, isoleucine, and valine is comprised between 0.1 and 0.4.

4. The method according to claim 1, wherein the weight ratio between (i) citric acid and (ii) the sum of malic acid and succinic acid is comprised between 1.0 and 4.0.

5. The method according to claim 1, wherein the citric acid: malic acid: succinic acid weight ratio is comprised between 10:1:1 and 2:1.5:1.5.

6. The method according to claim 1, wherein said active agent further comprises at least one amino acid selected from the group consisting of histidine, phenylalanine, methionine, tryptophan, tyrosine, and cysteine.

7. The method according to claim 1, wherein said active agent further comprises histidine, phenylalanine, methionine, tryptophan, and cysteine.

8. The method according to claim 1, wherein the ratio between (i) the overall molar amount of citric acid, malic acid, and succinic acid and (ii) the overall molar amount of methionine, phenylalanine, histidine and tryptophan is higher than 1.35.

9. The method according to claim 1, wherein the ratio between (i) the overall molar amount of citric acid, succinic acid, and malic acid and (ii) the overall molar amount of lysine and threonine is comprised between 0.10 and 0.70.

10. The method according to claim 1, wherein the weight or molar amount of citric acid is higher than the overall weight or molar amount of both malic acid and succinic acid.

11. The method according to claim 1, wherein the weight ratio between leucine and citric acid is comprised between 5 and 1.

12. The method according to claim 1, wherein said active agent further comprises histidine, phenylalanine, methionine, tryptophan, cysteine and tyrosine.

13. The method according to claim 5, wherein the citric acid: malic acid: succinic acid weight ratio is comprised between 7:1:1 and 1.5:1:1.

14. The method according to claim 5, wherein the citric acid: malic acid: succinic acid weight ratio is comprised between 5:1:1 and 3:1:1.

15. The method according to claim 7, wherein the ratio between 1 the overall molar amount of citric acid, succinic acid, and malic acid and (ii) the overall molar amount of lysine and threonine is comprised between 0.15 and 0.55.

16. The method according to claim 11, wherein the weight ratio between leucine and citric acid is comprised between 2.50 and 3.50.

17. A method of treating breast cancer in a subject comprising administering to the subject a) a therapeutically effective amount of an active agent, said active agent comprising leucine, isoleucine, valine, threonine, lysine, citric acid, succinic acid, and malic acid, and b) a therapeutically effective amount of doxorubicin, wherein the active agent and doxorubicin are administered simultaneously, separately or sequentially.

\*   \*   \*   \*   \*